United States Patent [19]

McCarty

[11] Patent Number: 6,099,869
[45] Date of Patent: Aug. 8, 2000

[54] CALCIUM TAURATE AND ANTIHYPERTENSIVE DRUG FOR HYPERTENSION

[75] Inventor: Mark F. McCarty, San Diego, Calif.

[73] Assignee: Nutrition 21, Purchase, N.Y.

[21] Appl. No.: 09/212,019

[22] Filed: Dec. 15, 1998

Related U.S. Application Data

[63] Continuation-in-part of application No. 08/943,370, Oct. 3, 1997, Pat. No. 5,876,757, and a division of application No. 08/554,151, Nov. 6, 1995, Pat. No. 5,776,498, which is a continuation-in-part of application No. 08/423,891, Apr. 18, 1995, Pat. No. 5,582,839.

[51] Int. Cl.$^7$ ...................... A61K 31/095; A61K 31/195
[52] U.S. Cl. ........................ 424/696; 514/711; 562/104
[58] Field of Search ........................... 424/696; 514/711; 562/104

[56] References Cited

U.S. PATENT DOCUMENTS

| | | | |
|---|---|---|---|
| 4,199,601 | 4/1980 | Durlach | 514/578 |
| 4,267,194 | 5/1981 | Durlach | 514/553 |
| 4,521,619 | 6/1985 | Kaplan | 514/315 |
| 5,582,829 | 12/1996 | McCarty | 424/489 |

FOREIGN PATENT DOCUMENTS

| | | |
|---|---|---|
| 7.241 M | 10/1989 | France . |
| 10059924 | 3/1998 | Japan . |
| 2111051 | 6/1983 | United Kingdom . |
| 2131025 | 6/1984 | United Kingdom . |

OTHER PUBLICATIONS

Dolara et al. Taurine–Calcium Interaction Measured by Means of 13C Nuclear Magnetic Resonance. Short Communication in: Biochemical Pharmacology, vol. 27. (1978) pp. 803–804.

Irving et al. 13C Nuclear Magnetic Resonance Study of ther Complexation of Calcium by Taurine. J. of Inorganic Biochemistry, vol. 13, pp. 137–150, (1980).

T.W. Anderson, et al. (1975) Ischemic heart disease, water hardness and myocardial magnesium. CMA Journal 113:199–203.

S.E. Atahanov, et al. (1992) Modulation of receptor–dependent increase of calcium ions in human platelets by taurine. Arzneim. –Forsch./Drug Res. 42(II):1311–1313.

J. Azuma, et al. (1983) Double–blind randomized crossover trial of taurine in congestive heart failure. Current Therapeutic Res. 34(4):543–557.

T.G. Brott, et al. (1992) Urgent therapy for stroke, Part I. Pilot study of tissue plasminogen activator administered within 90 minutes. Stroke 23:632–640.

B.S. Coller (1990) Platelets and thrombolytic therapy. The New England Journal Of Medicine 322(1):33–42.

T. Dyckner, et al. (1983) Effect of magnesium on blood pressure. British Medical Journal 286:1847–1849.

H.J. Gelmers, et al. (1988) A controlled trial of nimodipine in acute ischemic stroke. The New England Jouranl Of Medicine 318(4):203–207.

W. Hacke, et al. (1988) Intra–arterial thrombolytic therapy improves outcome in patients with acute vertebrobasilar occlusive disease. Stroke 19(10):1216–1222.

K.C. Hayes, et al. (1989) Taurine modulates platelet aggregation in cats and human. Am. J. Clin. Nutr. 49:1211–1216.

R.J. Huxtable (1992) Physiological actions of taurine. Physiological Reviews 72(1):101–163.

L.T. Iseri (1984) Magnesium in coronary artery disease. Drugs 28(Suppl. 1):151–160.

M. Malcangio, et al. (1989) Effect of ICV taurine on the impairment of learning, convulsions and death caused by hypoxia. Psychopharmacology 98:316–320.

T. Motoyama, et al. (1989) Oral magnesium supplementation in patients with essential hypertension. Hypertension 13:227–232.

A. Puca (1993) Thrombolysis in cerebral ischemia. A review of clinical and experimental data. Journal Neurosurg. Science 37:63–70.

S.M. Rothman (1983) Synaptic activity mediates death of hypoxic neurons. Science 220:536–537.

M.P. Ryan, et al. (1984) The role of magnesium in the prevention and control of hypertension. Ann. Clin. Res. 16:82–88.

S.W. Schaffer, et al. (1990) Regulation of calcuim homeostasis by taurine: role of calmodulin. Taurine: Functional Neurochemistry, Physiology, and Cardiology 217–225.

S.W. Schaffer, et al. (1994) Mechanisms underlying physiological and pharmacological actions of taurine on myocardial calcium transport. Taurine in Health and Disease 171–180.

A. Schurr, et al. (1987) Taurine improves the recovery of neuronal function following cerebral hypoxia: an in vitro study. Life Sciences 40:2059–2066.

M.S. Seelig, et al. (1974) Magnesium interrelationships in ischemic heart disease: a review. The American Journal of Clinical Nutrition 27: 59–79.

M. Shechter, et al. (1992) The rationale of magensium supplementation in acute myocardial infarction. Arch Intern. Med. 152:2189–2196.

Trust Study Group (1990) Randomised, double–blind, placebo–controlled trial of nimodipine in acute stroke. The Lancet 336;1205–1209.

B.C. White, et al. (1984) Brian ischemic anoxia. JAMA 251(12):1586–1590.

M.C.W. Wong, et al. (1990) Calcium antagonists: stroke therapy coming of age. Stroke 21(3):494–501.

*Primary Examiner*—Robert H. Harrison
*Attorney, Agent, or Firm*—Knobbe, Martens, Olson & Bear, LLP.

[57] ABSTRACT

Use of calcium taurate as an antihypertensive agent and dietary supplement. The compound is prepared by reacting taurine and calcium in a 2:1 molar ratio. The resulting mixture is diluted with alcohol and the remaining clear filtrate is crystallized. Calcium taurate is taken orally as nutritional supplement or antihypertensive agent, and can be used as an adjuvant to conventional antihypertensive drugs.

2 Claims, No Drawings

CALCIUM TAURATE AND ANTIHYPERTENSIVE DRUG FOR HYPERTENSION

RELATED APPLICATIONS

This application is a continuation-in-part of allowed U.S. Application Ser. No. 08/943,370, filed Oct. 3, 1997 now U.S. Pat. No. 5,876,757, and is a divisional of 08/554,151filed Nov. 6, 1995 now U.S. Pat. No. 5,776,498, which is a continuation-in-part of 08/423,891 filed Apr. 18, 1995 now U.S. Pat. No. 5,582,839, the entire contents of which are hereby incorporated by reference.

FIELD OF THE INVENTION

The present invention relates to the use of calcium taurate as a nutritional supplement and antihypertensive agent.

BACKGROUND OF THE INVENTION

Calcium is vital to normal bone formation and maintenance of bone density. Long-term dietary calcium insufficiency almost always results in net loss of calcium from the bones. The U.S. recommended daily allowance (RDA) for calcium is 800 mg/day, with an additional 400 mg advisable for pregnant and lactating women. A large proportion of the over-60 population consumes less than one-half of the RDA for calcium. This is also the age group most at risk of developing osteoporosis, which is characterized by loss of the organic matrix as well as progressive demineralization of the bone. Some studies suggest that postmenopausal women may need up to 1,200 mg calcium/day just to maintain calcium balance (*Textbook of Biochemistry With Clinical Correlations*, Second Edition, T. Devlin, Ed., John Wiley & Sons, New York, 1986, pp. 983–984).

Calcium has also been demonstrated to have an antihypertensive effect (McCarron, *Am. J. Clin. Nutr.* 65(suppl.):712S–716S, 1997). Calcium is also required for many enzymes, mediates some hormonal responses, and is essential for muscle contractility and normal neuromuscular irritability.

Taurine is an amino acid present in high concentrations in excitable and secretory tissue. Its role in cardiac function has received particular attention (Huxtable, *Physiol. Rev.*, 72:101–163, 1992; Schaffer et al., *Taurine in Health and Disease*, pp. 171–180, 1994). Although taurine can be synthesized endogenously from the amino acid cysteine, in mammals it is derived principally from the diet and is thus considered a "conditionally essential" nutrient. Conventional diets supply 40–400 mg of taurine daily, while vegetarian diets are extremely low in this amino acid.

The main function of taurine in mammals appears to be the regulation of transmembrane ionic movements, especially the regulation of calcium distribution (Schaffer et al., supra.; Huxtable, supra.; Schaffer et al., *Taurine: functional Neurochemistry, Physiology and Cardiology*, pp. 217–225, 1990). However, the mechanisms of this regulation are not well understood. Taurine has also been shown to have antihypertensive properties (Fujita et al., *Circulation* 75:525–532, 1987; Inoue et al., *Cardiovascular Res.*, 22:351–358, 1988). Taurine also exerts a platelet stabilizing effect both in vitro and, after oral administration, ex vivo (Hayes et al., *Am. J. Clin. Nutr.*, 49:1211–1216, 1989; Atahanov, *Arzneim-Forsch/Drug Res.*, 42:1311–1313, 1992). Acute intravenous administration of taurine reduces the incidence of arrythmias in animals treated with arrhythmogenic agents and multi-gram doses have been shown to be effective in the treatment of ischemic congestive heart failure (Azuma et al., *Curr Ther. Res.*, 34:543–557, 1983). Thus, increased taurine intake appears to be beneficial to vascular health.

Many sources of calcium, including calcium carbonate and calcium citrate, have less than optimal bioavailability. In addition, these sources of calcium require require an acidic environment for calcium release. Ordinarily, this does not present a problem. However, in individuals with achlorohydria, a condition in which stomach acid cannot be produced, these sources of calcium have very poor bioavailability because calcium ions cannot be released from the compounds. The present invention provides a calcium taurate complex for use as a dietary calcium supplement and antihypertensive agent. This complex has excellent calcium bioavailability and does not require an acidic environment for calcium release.

SUMMARY OF THE INVENTION

One embodiment of the present invention is a method for supplementing dietary calcium in an individual, comprising orally administering calcium taurate to the individual. Preferably, the calcium taurate provides between about 600 mg and 1,200 mg calcium. More preferably, the calcium taurate provides about 800 mg calcium.

Another embodiment of the present invention is a method of treating hypertension in an individual in need thereof, comprising administering an effective daily antihypertensive amount of calcium taurate to the individual. Preferably, the daily antihypertensive amount of calcium taurate provides between about 600 mg and about 1,200 mg calcium. More preferably, the daily antihypertensive amount of calcium taurate provides about 800 mg calcium.

The present invention also provides a pharmaceutical composition for treatment of hypertension, comprising an effective therapeutic dose of calcium taurate in conjunction with an antihypertensive drug. Preferably, antihypertensive drug is a diuretic, β blocker, calcium antagonist or angiotensin converting enzyme inhibitor.

DETAILED DESCRIPTION OF THE PREFERRED EMBODIMENTS

The present invention provides a calcium taurate salt for the nutritional and therapeutic administration of calcium and taurine, both of which are have beneficial antihypertensive effects. The calcium taurate complex dissolves rapidly and completely at acid, neutral or slightly alkaline pH, indicating extremely good bioavailability. This complex is particularly useful for administration to individuals unable to produce stomach acid because the calcium can be released at neutral and slightly alkaline conditions.

The reaction of taurine with calcium oxide, calcium hydroxide or calcium salts, under appropriate conditions, yields calcium taurate having the formula $(H_2N—CH_2—CH_2—SO_3^-)_2 Ca^{2+}$. This compound may be used both as a source of the essential nutrient calcium, and as a source of the conditionally essential amino acid taurine. The oral administration of these compounds delivers calcium and taurine to appropriate sites of action. Calcium taurate is also useful as a therapeutic agent for hypertension and can be used as an adjuvant to conventional antihypertensive drugs. There are four categories of antihypertensive drugs: diuretic agents (e.g., bendroflurnethiazide, chlorothiazide, cyclothiazide), β blockers (e.g., atenolol, propanolol), calcium antagonists (e.g., verapamil, nifedipine) and angiotensin converting enzyme (ACE) inhibitors (e.g., captopril, enalapril). A more complete listing of antihypertensive drugs may be found in *The Merck Manual*, 16th edition, pp. 422–425, 1992). The calcium taurate of the invention is highly soluble in water and provides excellent nutritional availability of both calcium and taurine.

The synthesis of calcium taurate is described in Example 1. Calcium hydroxide and taurine are mixed and heated in an aqueous solution, preferably water. Most of the water is removed by evaporation, and then alcohol is added to precipitate the product and allow it to be separated by filtration. The elemental analysis is provided in Table 1 and confirms isolation of a compound having the formula $(H_2N-CH_2-CH_2-SO_3^-)_2Ca^{2+}$. In addition, the $^1H$—NMR (500 MHz, $D_2O$) spectrum of calcium taurate showed the equivalence of the two methylene groups which resulted in one signal (type $A_4$) with the center at 3.029 ppm. The absence of other signals indicates that no degradation products were produced during the synthesis.

TABLE 1

Elemental analysis of calcium taurate

|  | % C | % H | % N | % S | % Ca |
|---|---|---|---|---|---|
| Calculated | 16.66 | 4.19 | 9.71 | 22.24 | 13.89 |
| 1st analysis | 16.61 | 4.38 | 9.35 | 19.34* | 13.35 |
| 2nd analysis** | 16.90 | 4.34 | 9.68 | 22.16 |  |

*Elemental analysis performed by Desert Analytics showed consistently less sulfur content due to potential calibration error.
**Repeated analysis of the same product performed by NuMega Resonance Labs confirmed the correct sulfur content in the product Since two taurine molecules combine with one calcium atom, it is preferred that the molar ratio of taurine to calcium be about 2:1, although ratios of between about 1.5:1 and about 2.5:1 are contemplated. The product is extremely water soluble.

For oral administration as a nutritional supplement or antihypertensive agent, calcium taurate may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and such compositions may contain one or more of the following agents: sweeteners, flavoring agents, coloring agents and preservatives. The sweetening and flavoring agents will increase the palatability of the preparation. Tablets containing the calcium taurate in admixture with non-toxic pharmaceutically acceptable excipients suitable for tablet manufacture are acceptable. Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets may be uncoated or coated by known techniques to delay disintegration and absorption in the gastrointestinal tract and thereby provide a sustained release and sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the calcium taurate in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

The pharmaceutical compositions may also be in the form of oil-in-water emulsions. The oily phase may be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

In a preferred embodiment, the amount of calcium taurate administered orally as a dietary supplement or therapeutic agent, either alone or as an adjuvant to one or more antihypertensive drugs, is between about 6 g and about 12 g daily, corresponding to between about 600 and 1,200 mg calcium, the remainder being taurine. In a particularly preferred embodiment, the amount of the complex administered daily is about 8 g, corresponding to about 800 mg calcium (the U.S. RDA). The preferred administration schedule for delivery of 800 mg calcium is two tablets, twice daily. If one were to ingest another high-availability source of calcium plus straight taurine to achieve analogous benefits, eight tablets daily would be needed which is hardly optimal from a compliance standpoint.

It is evident that many variations of the synthetic procedure described below may be used to generate the compounds of the present invention. Any such protocol resulting in the production of calcium taurate is within the scope of the present invention.

Example 1

Preparation of Calcium Taurate

A vigorously stirred suspension of calcium hydroxide (7.4 g, 0.1 mol) in water (50 ml) was boiled for 15 minutes. Taurine (25 g, 0.2 mol) was added to this hot suspension and the mixture was stirred for an additional 15 minutes. The resulting cloudy solution of calcium taurate was filtered, and the water was removed under reduced pressure. The resulting wet crystals were treated with ethanol (50 ml) to complete crystallization. Calcium taurate was collected by filtration, washed with ethanol and dried under vacuum. The amount of calcium taurate obtained was 27.5 g (95% yield). Elemental analysis (Table 1) and NMR spectroscopy confirmed the identity of the compound.

The above detailed description of the invention is set forth solely to assist in understanding the invention. It is to be understood that variations of the invention, including all equivalents now known or later developed, are to be considered within the scope of the invention, which is limited only by the following claims

What is claimed is:

1. A pharmaceutical composition for treatment of hypertension, comprising an effective therapeutic dose of calcium taurate, wherein the ratio of taurine to calcium is between 1.5:1 and about 2.5:1, in conjunction with an antihypertensive drug.

2. The pharmaceutical composition of claim 1, wherein said antihypertensive drug is a diuretic, β blocker, calcium antagonist or angiotensin converting enzyme inhibitor.

* * * * *